United States Patent
Newman

(10) Patent No.: US 8,740,764 B1
(45) Date of Patent: Jun. 3, 2014

(54) EXERCISE APPARATUS EMPLOYING MAGNETS FOR THERAPEUTIC AND EXERCISE BENEFIT

(76) Inventor: Geraldine Newman, New York, NY (US)

(*) Notice: Subject to any disclaimer, the term of this patent is extended or adjusted under 35 U.S.C. 154(b) by 1643 days.

(21) Appl. No.: 11/731,402

(22) Filed: Mar. 30, 2007

Related U.S. Application Data

(60) Provisional application No. 60/842,717, filed on Sep. 7, 2006.

(51) Int. Cl.
*A61N 2/00* (2006.01)

(52) U.S. Cl.
USPC .................................. 600/13; 600/9; 482/903

(58) Field of Classification Search
USPC .......................... 600/9–15; 482/903; 128/897; 601/DIG. 4, 15, 23–26
See application file for complete search history.

(56) References Cited

U.S. PATENT DOCUMENTS

| | | | | |
|---|---|---|---|---|
| 4,587,956 A | * | 5/1986 | Griffin et al. | 600/15 |
| 5,014,981 A | * | 5/1991 | Prelich | 482/108 |
| 5,626,545 A | * | 5/1997 | Newman et al. | 482/127 |
| 5,810,696 A | * | 9/1998 | Webb | 482/52 |

* cited by examiner

*Primary Examiner* — Charles A Marmor, II
*Assistant Examiner* — Carrie R Dorna
(74) *Attorney, Agent, or Firm* — Andrew S. Langsam; Pryor Cashman LLP

(57) ABSTRACT

An exercise device having therapeutic properties is provided. The device includes a first element and a second element relatively movable with respect to the first element. A resistance-generating mechanism links the first and second elements to impede the relative motion of the first and second elements so that the user must exercise or expend energy to overcome the resistance of the first and second elements. A first magnet is disposed in at least one of the first or second elements in a location where a user's body part contacts the first or second element during use. The magnetic field of the first magnet is directed into the user's body part for therapeutic effect, preferably from the north pole of the magnet. A second magnet or set of magnets may be employed for therapeutic effect and/or to increase the resistance of the device by using magnetic interaction (either attraction or repulsion) to further impede the relative motion of the first and second elements.

3 Claims, 4 Drawing Sheets

EXERCISE APPARATUS EMPLOYING MAGNETS FOR THERAPEUTIC AND EXERCISE BENEFIT

RELATED APPLICATIONS

Domestic priority is claimed from U.S. provisional patent application No. 60/842,717 entitled "Method of Using Magnets for Therapeutic and Exercise Benefits and Apparatus Employing Same," filed Sep. 7, 2006.

BACKGROUND OF THE INVENTION

1. Field of the Invention

The invention relates to exercise devices, and more specifically to exercise devices that offer the user rehabilitative and therapeutic effects. Magnets embedded into a device worn by an individual are believed to provide a therapeutic effect to the wearer and thus embedding magnets into an exercise device is believed to provide a synergistic exercise device, which provides a rehabilitative component and an additional resistive force to the exercise device.

2. Description of the Related Art

Regular exercise is considered essential for a person's individual health and well being. It is believed to provide life-long benefits. Many types of mechanical devices and apparatuses have been developed for the purposes of allowing the individual to exercise one or more parts of his/her body to promote muscle strength, tone, flexibility, and the like. Three such devices are described in U.S. Pat. Nos. 5,626,545, 5,713,822, and 6,013,015 of which I am the co-inventor, the teachings of which are expressly incorporated herein by reference. These devices, like many, provide a resistance force which the user is intended to overcome by flexing/extending (or abducting/adducting) one or more muscles and/or muscle groups. Typical exercise devices found in the home or in professional-like exercise locations, namely, gyms, spas, work-out rooms, etc. use weights, a weight and pulley system, flexible rubber-like bands, and/or spring mechanisms, all for generating resistive forces. Other devices exist, too. The user is meant to overcome these forces in a repetitive fashion, i.e., by doing "sets" or repetitions of overcoming the resistant forces, thereby building up the quality, tone, flexibility, strength, etc. of his or her muscles and/or muscle groups. However, such devices can be considered limited in scope, in that they generally have, for each repetition or set, a predetermined and fixed amount of resistance for the user to overcome. For example, in the above mentioned U.S. patents, the devices all use resilient devices such as compression springs or elastic-like cords that provide limited amounts if any in variation of the resistance force required to be overcome by the user in a repetition cycle. The present invention provides an exercise device which uses the magnetic flux and attractive or repulsive forces between magnets (or between a magnet and a piece of ferro-magnetic material) as a mechanism to both provide a variation in the resistance force to be overcome during a set or repetition of the exercise device and, at the same time, provide the therapeutic effect considered to be provided by magnets, when the magnetic field comes into contact with the user's body. Additionally, exercise devices are frequently used to rehabilitate and/or revive injured tissue.

Unrelatedly, it has been discovered that magnetic fields have a therapeutic effect on living tissue; specifically, when an injured tissue is placed within a magnetic field, preferably a field from a north pole of a magnet, the healing process is believed to be enhanced, even accelerated.

Although exercise devices and magnets have both been individually employed to rehabilitate tissue and promote general well being, there is a long felt need for the combined use of both of these therapeutic methods at substantially the same time in a single device.

SUMMARY OF THE INVENTION

The invention is an exercise device having both mechanical resistance for the user to overcome while using one or more muscles or muscle groups, as well as magnetic fields that interact with the user. The magnetic fields can even cooperate with the resistance provided by the exercise device.

Generally the invention is an exercise device having a first element and a second element relatively movable with respect to the first element. A resistance-generating mechanism links the first and second elements to impede the relative motion of the first and second elements. A first magnet or set of magnets is disposed in at least one of the first or second elements in a location where a user's body part contacts the first or second element during use, so that a magnetic field of the first magnet is directed into the user's body part. The invention preferably further includes a second magnet or set of magnets, a first portion of the second set being disposed on the first element and a second portion of the second set being disposed on the second element in a location so that the magnetic interaction between the first and second portions further impedes the relative motion of the first and second elements. It is preferred that the first magnet is disposed with its north pole facing the user's body part.

In one embodiment, the invention is a thigh abduction machine, the resistance-generating mechanism is a spring, and the first magnet is at least one magnet disposed in an inner-facing surface of at least one of the first or second elements where a user's thigh contacts the first or second element. Additionally, should the second magnet or set of magnets be employed, the first portion of the second set is disposed in a first segment of the first element, and the second portion of the second set is disposed in a second segment of the second element that overlaps the first element. Alternatively, a second magnet may be disposed on the first element, and a ferromagnetic material may be disposed on the second element in a location so that the magnetic interaction between the second magnet and the ferromagnetic material further impedes the relative motion of the first and second elements.

In another embodiment, the device is a hand grip, the resistance-generating mechanism is a spring, and the first magnet comprises at least one magnet disposed in an outer-facing surface of at least one of the first or second elements where a user's hand contacts at least one of the first or second element. In such embodiment, the second magnet may include one or more magnets facing each other with like poles on the free ends of the grip member elements to thereby add to the resistance needed to be overcome while squeezing the hand grip.

Regarding the second magnet or set of magnets, the first and second portions of the second set of magnets may have like poles facing each other to generate a repulsive magnetic interaction to impede relative motion of the first and second elements. Or, alternatively, the first and second portions of the second set of magnets may have opposite poles facing each other to generate an attractive magnetic interaction to impede relative motion of the first and second elements.

The invention includes at least one element that is movable with respect to another element and a resistance-generating mechanism linking the two which impedes the movement of one element with respect to the other. The user places a body part, for example, their outer thigh, in contact with one or more of the movable elements and pushes or pulls the elements apart or together (i.e., moving one element with respect to another) against the resistance force, thereby exercising the relevant muscles and/or rehabilitating the relevant tissue.

The movable elements i.e., in the preferred embodiment the thigh engaging members, each also include one or more magnets in one of several locations. First, magnets may be disposed along the portion of the movable element that directly contact the body part. In this way, the magnetic field generated by the magnets encounters and may even be in direct contact with the body tissue and promotes well being/healing. It is preferred that such magnets are oriented so that the north pole of the magnets is in contact with or facing the relevant body part.

Second, magnets may also be disposed in a secondary location other than that which necessarily contacts the exercising body part. One such preferred secondary location would include areas of the movable elements that are in close proximity to one another (i.e., a first portion of the first movable element that is substantially close to or contacting a corresponding portion of the second element). For these secondary magnets, it is preferred that one movable element have its magnets facing in one direction and the other movable element have its secondary magnet facing in the proper direction so as to increase the resistive forces required to be overcome in operating the device. For example, in a device where two elements are intended to be pulled apart, the respective two magnets on the two elements have opposite poles facing each other so that, when the two elements are close to each other or in contact with each other, their respective magnets attract each other (since opposite poles of magnets attracts). Likewise, for devices where two elements are intended to be pushed together, the two secondary magnets in question have like poles facing each other so as to repel each other when they are brought close together. In this way, not only must the user overcome the mechanical resistance force generated by the conventional resistance force-generating element of an exercise device but the user must also overcome the attractive forces of the north and south poles of the respective magnets. Furthermore, it is believed that as the distance between the magnets increases or decreases, depending upon the type of exercise device, the attractive and repulsive forces of the respective magnets varies and this provides a changing overall resistance to the exerciser, even though the mechanical resistance is fixed for each mechanical repetition.

Each movable element may be provided with recesses or receptacles for receiving one or more magnets in different locations along the contact surface area with the body. That is, different strength magnets may be inserted and removed from the various movable elements for providing different therapeutic benefits to the user for different locations. Additionally, the secondary attracted or repulsive magnets may also be removable and may be replaced with different magnets of varying strength.

The above embodiments imply that permanent magnets may be employed in the inventive device. However, electromagnets may also be employed for both the primary therapeutic magnets as well as the secondary attractive or repelling magnets.

DETAILED DESCRIPTION OF THE INVENTION, THE PREFERRED EMBODIMENT, BEST MODE AND THE DRAWINGS

Description will now be given of the invention with reference to the attached FIGS. 1-7. It should be understood that these figures are exemplary in nature and in no way serve to limit the scope of the invention, which is defined by the claims appearing hereinbelow.

Figure 1:
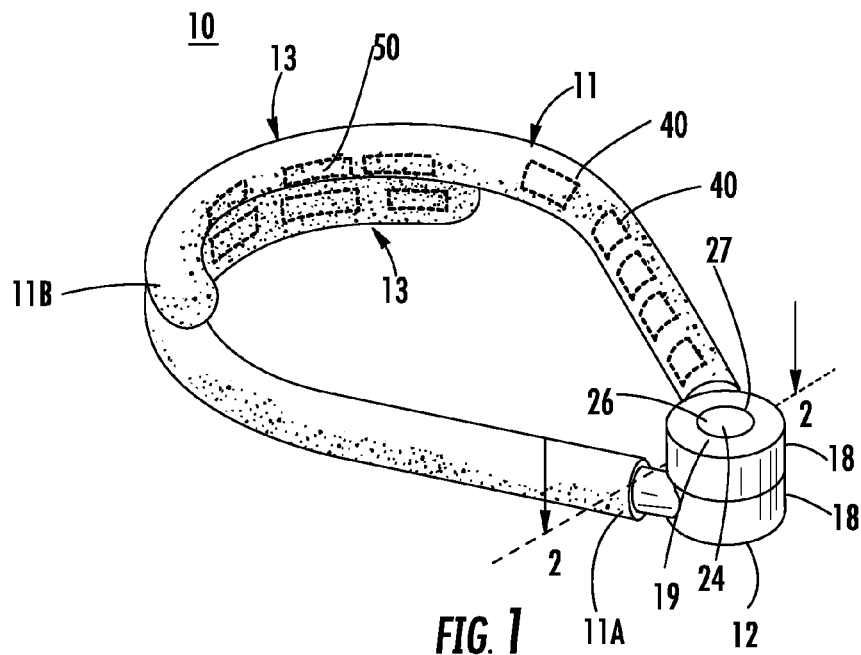
FIG. 1 is a perspective view of a first embodiment of the present invention.
Figure 2:
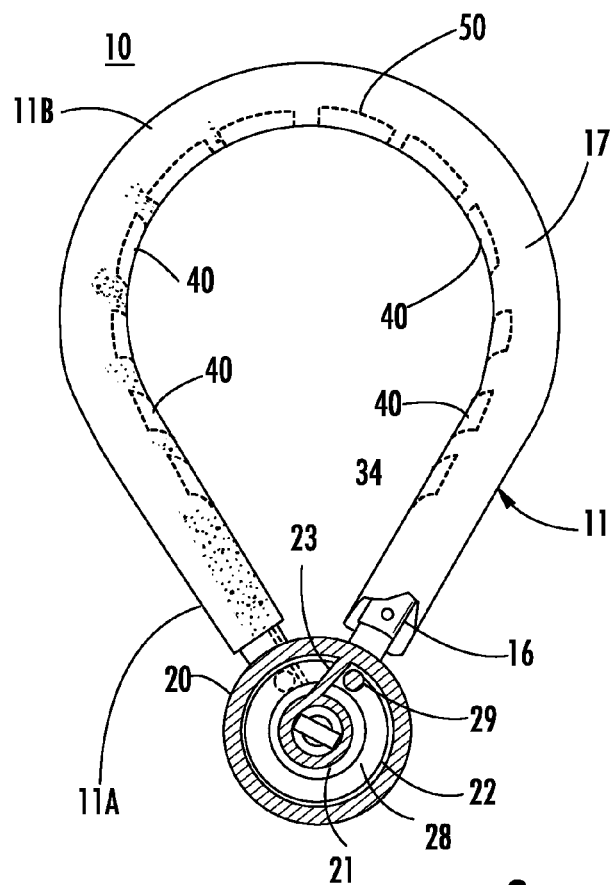
FIG. 2 is a partial sectional top plan view of the embodiment of FIG. 1.

Referring now to the drawings, particularly FIGS. 1-4 thereof which illustrate a first embodiment of the present invention, the reference numeral 10 generally designates the improved exercise device shown as being applied to the thighs T (see FIGS. 3 and 4) of an exercising person employing device 10. The teachings of the exercise devices of which I am the inventor, mentioned and identified above, are expressly incorporated herein. The exercise device 10 includes a pair of thigh-engaging hook-shaped members 11 hingedly joined at their inner (or non-curved) ends by a spring-loaded hinge member 12. The spring loaded hinge is adapted to resiliently urge hook members 11 to a contracted or closed condition, as shown in FIGS. 1 and 2. Thus, the outward pushing of the user's thighs, against the spring's force, will result in the user working or exercising against the spring force and, hopefully for the user, provide muscle tone, rehabilitation, and/or exercise.

Each of the hook members 11 includes a curved section 13 terminating at its inner end in a longitudinally extending linear leg 14. Each hook member 11 is formed of a rigid, preferably metal or stiff and strong plastic core section 16 open at its inner end and closed off and rounded at its outer end (as viewed in FIGS. 1-4). Preferably, a large portion of the hook members, at least to the extent the same are in contact with the body of the exerciser, are covered by a thick soft plastic, foam or elastomeric sheath 17. The sheath 17 covers the closed off end of the hook members and, in the preferred embodiment, terminates proximal to the end of the inner end of core member 16, near the hinge 12.

Hinge member 12 includes a pair of coaxial cylindrical knuckles 18 closed at their outer ends by annular walls 19 and provided with coaxial end-to-end skirt walls 20 whose end edges are in mutual slidable and rotatable engagement. Projecting inwardly from the inner periphery of each annular wall 19 is an axial tubular section 21 which delineates with skirt walls 20 an axially extending annular cavity 22, the confronting outer and inside faces of each respective pair of skirt wall 20 and tubular wall or annular cavity 22 being connected by a stop defining short radial wall 23 joining a respective annular end wall 19. Outwardly, facing peripheral shoulders are formed on the inside peripheral faces of tubular sections 21 and the axial bore delineated by tubular wall 21 is rotatably engaged by a hinge pin 24 having enlarged end heads 26 bearing on the aforesaid peripheral shoulders to releasably and rotatably interlock knuckles 18. The open outer ends of tubular walls 22 are closed by respective plugs 27. Of course, this is just one embodiment of the present invention and the present invention can be associated with one or more other exercise devices which use spring, mechanical, rubber bands, or other forms of resistance for muscle rehabilitation, exercise, and health.

Figure 4:
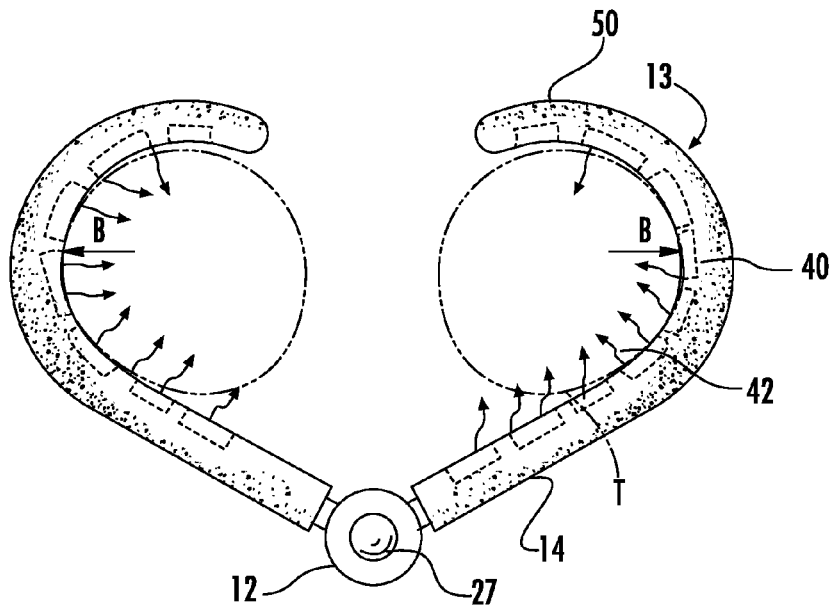
FIG. 4 is a view similar to that of FIG. 3 showing the device expanded to its open configuration by the outward movement of the user's thighs against both the interior, resistive force of the spring and the attractive forces of the embedded magnets.

Housed in the annular cavity 22 and coaxial with encircling tubular walls 21 is a helical torsion spring 28 terminating at opposite ends in radially offset longitudinally projecting end legs 29. The torsion spring 28 is so oriented and stressed that, in the unused condition of exercise device 10, it biases the exercise device to a closed or contracted configuration (FIGS. 1 and 2) with the free ends of curved sections 13 overlapping and yet being axially offset. The opening circumscribed by the hook members 11 is generally pear- or light bulb-shaped when the hook members 11 are in the closed contracted configuration (as easily seen in FIG. 2), and generally heart-shaped when hook members 11 are in the opened operating configuration during exertion of force by the outward movement of the user's thighs, for example (as shown in FIG. 4) against the force of the internal torsion spring.

A first set of magnets 40 are lined upon, preferably embedded, along at least a portion of the straight portion of hook members 11 closer to their respective proximal end 11A where the user's thighs come into closest contact with hook member 11. Thus, the first set of magnets are directed inwardly, toward the user's thighs. Magnets 40 (preferably small circular magnets) generate magnetic field lines of flux 42 (see FIGS. 3 and 4). The magnets may actually contact and the magnetic field is intended to contact and somewhat penetrate the tissue of the user's thighs, when in exercising use. Magnets 40 are preferably oriented with their North poles facing inwardly towards the user's thighs for believed optimal therapeutic effect.

A second set of magnets 50 (see FIGS. 1 and 3) are lined upon or embedded along at least a portion of the distal or curved end 11B of hook members 11. This set, too, is directed inwardly, i.e., towards the user's thighs. This set of magnets overlap one another in the closed configuration as shown in FIGS. 1 and 2. While secondary magnets 50 may add to and also provide therapeutic benefit to the user (as magnets 40), their primary purpose is to increase the resistive forces (arrows A in FIG. 3) that the user must overcome in opening the device (arrow B in FIG. 4). The second set of magnets are thus configured to be attractive to one another to force the user to exercise and work against the attractive magnetic forces. Preferably, magnets 50 of one or the first hook member 11 are arranged to have their opposite poles facing the magnets 50 of the other or the second hook member 11 so as to cause an attractive force between the two hook members 11.

Figure 6:
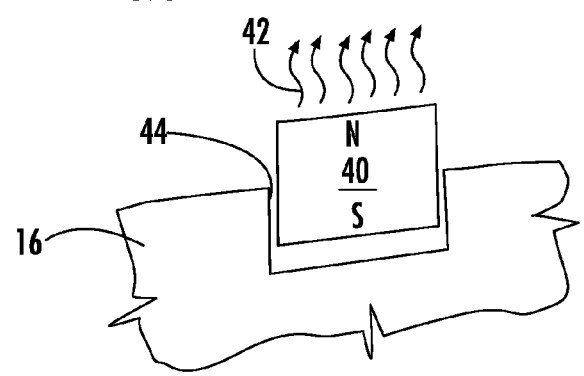
FIG. 6 is a partial, side schematic of a removable and replaceable magnet for a section of an exercise device in accordance with the invention.
Figure 7:
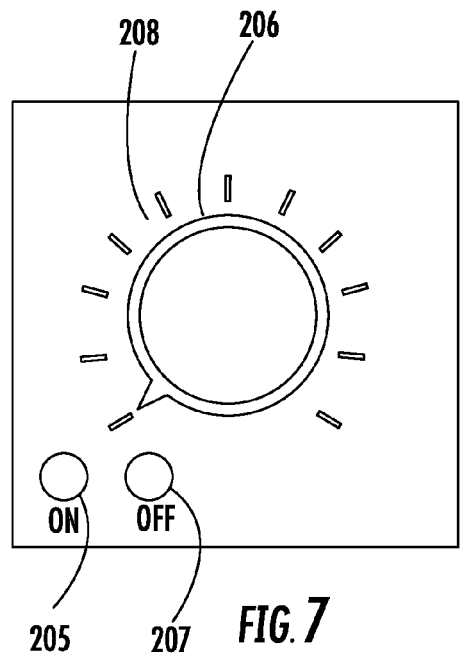
FIG. 7 is a schematic of a control panel for use with an electromagnetic embodiment of the invention.

Both sets of magnets 40 and 50 may be permanently embedded into core sections 16 at the appropriate locations. Alternatively, as shown in FIG. 6, the magnets may be disposed (adhered, screwed or otherwise maintained) in recesses 44 and removable by the user for the purposes of varying the size, strength and/or amount of therapeutic magnetic field applied to the user's body by magnets 40 and/or varying the amount of resistive forces generated by magnets 50. In one embodiment the recesses are made of ferromagnetic material so as to hold the magnets therein so that no other mechanical holding mechanism is required. The inventive exercise device may be sold with multiple replacement sets of magnets to give the user the flexibility of varying the field intensity of the magnets and their location(s). As another alternative, instead of permanent magnets, magnets 40 and/or 50 may be electromagnets in communication with an internal power supply, i.e., self-contained batteries and appropriate wiring may be provided within the tubular or hollow sections of the hook members or an external power supply (not shown) and preferably equipped with a control pad for turning the magnets on and off as well as varying their field intensity may be used. An exemplary control pad 200 is shown in FIG. 7, which has ON and OFF buttons 205, 207 as well as a varistor-type knob 206 with a corresponding intensity/power scale 208.

Figure 3:
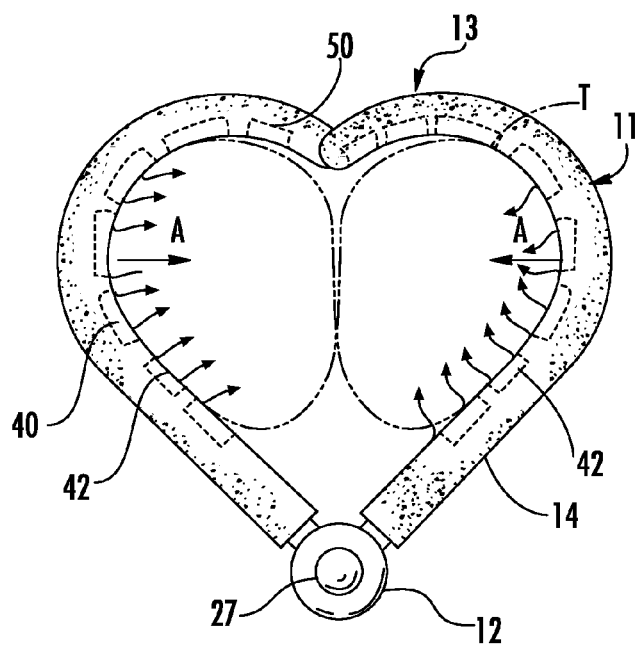
FIG. 3 is a top plan view of the embodiment of FIGS. 1 and 2 in a substantially contracted configuration as applied around the thighs of a user.

In the application and operation of exercise device 10, the hook members 11 are rotatably separated about hinge 12 against the influence of both torsion spring 28 and the attractive forces generated by magnets 50 to an open position and slid forwardly over the thighs T in their contracted condition and then released to permit the hook members 11 to contract and tightly engage the opposite outer surfaces of thighs T and urge them together in the direction of arrows A as shown in FIG. 3. The thighs T are then abducted in the direction of arrows B against the contraction influence of curved sections 13 which increases in its contraction pressure with the separation thereof and the increased loading of torsion spring 28 as well as against the attractive forces of magnets 50. The exercise is continued by the repetitive abduction and adduction of thighs T against the contraction influence of the hook members 11 to exercise the thighs T and buttocks in an optimal manner. At the same time, magnets 40 provide therapeutic and healthful magnetic field energy to the tissues of the user's thighs. Thus magnets 40 are therapeutic while magnets 50 may be both therapeutic and provide increased resistance to the pulling apart of the hook members 11 by the user. Of course, in an embodiment of the invention, the magnets 40, alone, may be provided so that the exercise device is providing therapeutic effect by the cooperation of the magnets and the user's skin while the mechanical resistance is solely provided by the spring, rubber or elastic bands, the use of purely mechanical resistance for muscle rehabilitation and toning.

Figure 5:
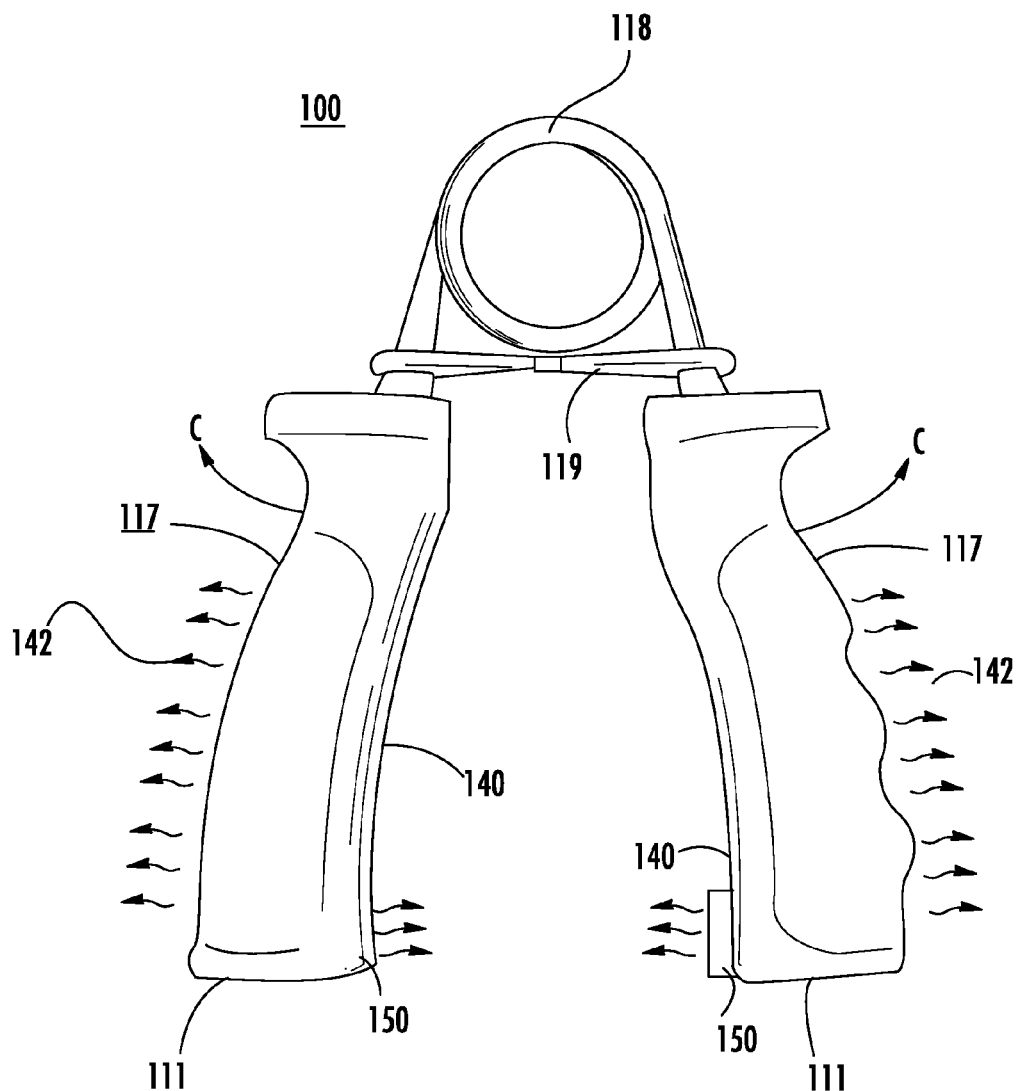
FIG. 5 is a top plan view of a second embodiment of the present invention as used for a hand grip exercise device.

FIG. 5 shows a second embodiment of the invention. Device 100 is a handgrip-style exercise device having two hand grip members 111. A contoured section 117 is provided for optimal finger grip and thumb placement. The two grip members 111 are connected via spring member 118 which tends to urge grip members 111 apart in the direction of arrows C. Hook 119, preferably an S-hook, retains grip members 111 and prevents them from being urged too far apart by spring member 118 (otherwise it would be difficult for the user to get his or her hand around the two grip members and their proper relative orientation would be compromised).

Magnets 140 are preferably embedded in grip members 111 below contoured sections 117. Magnets 140 generate a therapeutic magnetic field 142 which contacts and somewhat penetrates the tissues of the user's hand. As in the embodiment described above, it is preferred that magnets 140 have their north poles facing outward towards the user's hand tissue. This is believed to provide the desired and beneficial therapeutic effect. Additionally, magnets 150 may be provided on the inside and proximal to the free ends of grip members 111. A second set of one or more magnets 150 are preferably oriented so that the same poles face each other (i.e., north facing north or south facing south). Since like poles repel, as the user squeezes the hand grip 100, the second set of magnets 150 are brought closer together, and the repulsive magnetic forces generated by the interaction of magnets 150 increases. This repulsive force is supplemental to the mechanical force provided by the spring 118, as the hand grips are moved together by the user's exercise. As above, the various magnets 140 and 150 in device 100 may be permanently integral with the grip members or may be made in a replaceable manner. Also, magnets 140 and 150 may be either permanent or electromagnetic in nature.

Figure 8:
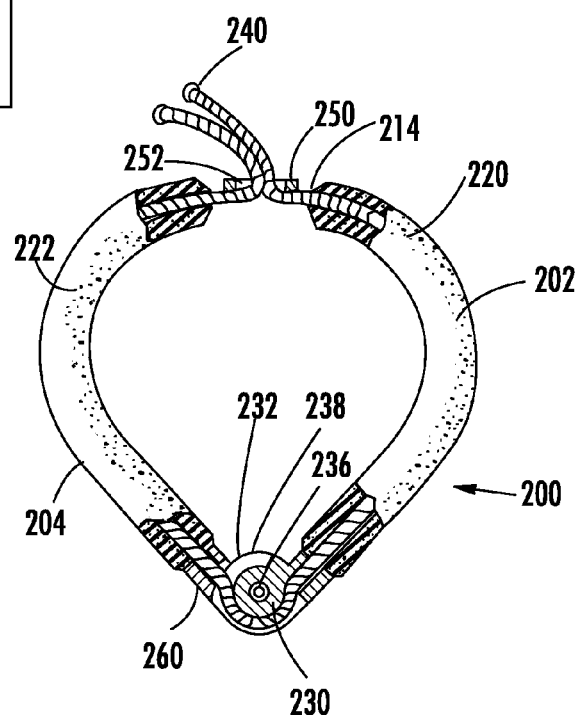
FIG. 8 is a top elevational, partial cut-away view of another embodiment of the invention.
Figure 9:
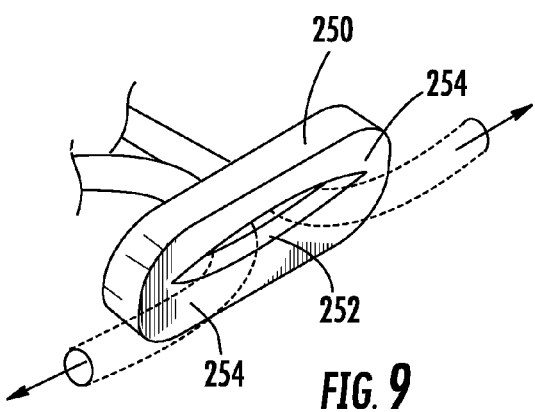
FIG. 9 is a perspective view of a portion of the exercising device shown in FIG. 9.

Although exercise devices 10 and 100 are illustrated as being applicable to a person's thighs and hands, the invention may be employed in any type of exercise or rehabilitative device to enhance the exercise and/or healing of other parts of the body as well. See, for example, another embodiment of the invention as depicted in FIGS. 8 and 9. This embodiment and others, correspond to the basic exerciser depicted and described in my prior U.S. Pat. No. 5,626,545, the description and drawings of which are herein incorporated by reference. However, now, I have invented, as described herein, a synergistic or enhanced exercise device which uses a conventional mechanical resistance element, for example, the spring, as described above, a bungee cord (as described and shown with reference to FIGS. 8 and 9) a spring held between the free ends of the hooked shaped devices, as shown in other Figs. of the '545 patent and/or other exercising devices. Indeed, the present invention is not limited to exercise devices which use resistance forces for muscle rehabilitation and conditioning and could be adapted for use in any exercise device which allows contact of the device with the user and the possibility of providing close body contact with the magnetic forces of the therapeutic magnets to contact the body and/or for the magnetic flux to penetrate the skin surface of the user, during muscle treatment.

In the preferred embodiment, however, the invention contemplates that the magnetic therapeutic effect of the first magnetic set acts at the same time as the conditioning of the muscle(s) of the user by use of the mechanical exercise device which operates against the force of a spring, a weight and pulley system, flexible rubber-like bands, bungee cord, or other resistive forces. Not only simple mechanical devices having only one or two moving parts are contemplated; any exercise device which has a part that is in contact with the user's body may be provided with the synergistic and enhancing/therapeutic magnets of the invention. Also, although a series of small magnets are shown in the drawings illustrating the first embodiment (FIGS. 1-4, 6) and a single bar magnet is shown in the drawing illustrating the second embodiment (FIG. 5), any convenient shape of magnet or combinations of magnets may be utilized for either the first set of (therapeutic) magnets or the second (resistance-enhancing) magnets. The second set of magnets is preferably a means to both provide some additional level of therapeutic effect to the user and, in addition, some measure of varied and additional resistance, i.e., an added component to the mechanical resistance provided by the other mechanical aspects of the exercise device.

FIG. 8 shows another embodiment of the invention where the mechanical spring is replaced by a continuous bungee-like cord passing through the curved arms of the device, i.e., a highly resilient and strong elastic rope 214 passes within the center of the two hooked-arms 202 and 204 are secured by a holding device 250 for the free ends of the bungee cord (see FIG. 9). The clamp arms 202 and 204 are supported for swinging in a common or parallel planes by a hinge member 230. The clamp members 202 and 204 have confronting concave faces and are relatively swingable between a contracted condition with their free ends proximately spaced and an expanded condition with their free ends increasingly separated. This embodiment shows the clamp arms of the exerciser such that, in the closed configuration, i.e., without the exertion of force by the user, the arms are not overlapping of one another. Just as in the prior embodiments, magnets can be provided to the clamp arms to allow for the user's body to come into contact with the magnetic field provided by the magnets on the clamp arms. Also, just as in the prior embodiment, a second set of magnets can be provided to the clamp arms for changing the resistance of the device, as the user uses the same for exercise. The magnets for this purpose may need to be stronger to provide attraction to one another so that the user exercises against the attractive forces of the second set of magnets of the exerciser.

The hinge member 230 includes a pair of axially spaced integrally joined outer circular discs rotatably sandwiching an inner disc 232, the outer discs being rotatably joined by a pivot pin 236, a peripheral guide groove 238 being formed in the face periphery of one of the discs. A socket member extends radially from and is integrally formed with inner disc 238 and a socket member 260 is integrally formed with and projects radially from the pair of discs, the socket members having outwardly facing openings.

Each of the clamp arms include a rigid tubular plastic lined metal core having an internal plastic lining terminating at its outer end in an annular lip overlying the outer end of each metal core. The inner end of each metal core telescopes and is firmly secured in a respective socket member. A soft compressible sponge sheath, formed of natural or synthetic rubber, covers each of the tubular metal cores. An elastomeric cord 214 preferably including a core of natural or synthetic rubber is covered by a braided fibrous tubular sheath. The elastomeric cord transverses the clamp arm tubular cores and its medial portion extends along the peripheral groove. The outer ends of the cord project beyond the free ends of clamp arms 202 and 204 and hooked ends of the arms 220 and 222 and terminate in knots 240. A loop shaped coupling member 250 (see FIG. 9) has a longitudinally extending opening or slot 252 with longitudinally converging confronting end faces delineating wedge shaped slots 254. The free outer ends of the cord 214 are releasably and firmly engaged or wedged in the respective wedge slots 254 to permit the adjustment of the length of the elastomeric cord 214 extending between the clamp arms. This, of course, adjusts the resistance of the mechanical exercising device.

The operation and application of the exercise device shown in FIGS. 8 and 9 are similar to those of the earlier described embodiments, elastomeric cord 214 being functional to bias the clamp arms 202 and 204 to their contracted condition and releasably coupling member 250 permitting the adjustment of such bias and resistance and the release of the ends of the cords to facilitate the application of the device to the thighs of the user.

Device 200 and the clamp arms 202 and 204 are biased to their closed condition by the elastomeric or bungee cord 214, instead of the helical torsion spring shown in the prior embodiments. Specifically, the modified exercising device 200 of FIGS. 8 and 9 include a pair of thigh engaging rigid tubular hook shaped clamp members 220 and 222 supported for swinging in a common or parallel set of planes.

The invention is not limited to the above description or even to the embodiments shown in the attached exemplary drawings but rather by the claims appearing hereinbelow as well as equivalents thereof. Modifications apparent to one skilled in the art are considered to be within the scope of the invention.

What is claimed is:

1. An exercise device for the thighs of a human, comprising:

a first element, adapted in curvature to guide along and contact at least a large part of the outside of one of the human's thighs;

a second element connected to and yet relatively hingedly movable with respect to said first element, also adapted in curvature to guide along and contact at least a large part of the opposed and outside of the other of the human's thighs;

a muscular resistance-generating mechanism linking said first and second elements to impede the relative hinged outward motion of said first and second elements as thighs are moved outwardly with respect to one another and to thereby exercise the thigh muscles during such motion against said resistance-generating mechanism;

a first set of magnets disposed in and extending along a substantial length of said first and second elements in a location directly adjacent to a large portion of the thighs, the thighs held by said elements during exercise and directed inwardly toward the thighs, said magnets adapted to provide depth of penetration of magnetic lines of flux directed into and along the muscles in the thighs being exercised by said exercise device, such that the magnetic lines of flux of said sets of magnets are adapted to penetrate into the muscles of the thigh of said human for providing efficacious and not insignificant, mere surface magnetic therapeutic effect during exercise;

a supplemental and second set of magnets disposed on at least said first or said second element; and a ferromagnetic material disposed on the other of said first or said second element in a location so that the attractive magnetic interaction between said supplemental and second set of magnets and said ferromagnetic material is adapted to provide a gradation in the resistance force to be overcome during a repetition of the exercise device while opening and closing the thighs, separately yet simultaneously with said magnetic lines of flux penetrating said thighs.

2. An exercise device according to claim 1, further comprising a power supply, wherein at least one of said first or second set of magnets are of an electromagnet nature and powered by said power supply.

3. An exercise device according to claim 2, further comprising a control for activating said power supply of said at least one first or second set of magnets and for varying the magnetic field intensity of said at least one first or second set of magnets.

* * * * *